United States Patent
Cavell et al.

(10) Patent No.: US 6,492,474 B2
(45) Date of Patent: Dec. 10, 2002

(54) ALUMINUM COMPLEXES FOR OLEFIN POLYMERIZATION

(75) Inventors: Ronald G. Cavell, Edmonton (CA); Qinyan Wang, Calgary (CA); Ruppa P. Kamalesh Babu, Edmonton (CA); Aparna Kasani, Edmonton (CA)

(73) Assignee: The Governors of the University of Alberta (CA)

( * ) Notice: Subject to any disclaimer, the term of this patent is extended or adjusted under 35 U.S.C. 154(b) by 0 days.

(21) Appl. No.: 09/809,474

(22) Filed: Mar. 15, 2001

(65) Prior Publication Data

US 2001/0018534 A1 Aug. 30, 2001

Related U.S. Application Data

(62) Division of application No. 09/375,618, filed on Aug. 17, 1999, now Pat. No. 6,235,919.

(51) Int. Cl.$^7$ .............................. C08F 4/06; B01J 31/00; C07F 5/06; C07F 9/02
(52) U.S. Cl. .................. 526/126; 502/103; 526/131; 526/134; 526/154; 526/352; 556/174; 556/176; 556/178
(58) Field of Search ................................ 556/174, 176, 556/178; 502/103; 526/126, 131, 134, 154, 352

(56) References Cited

U.S. PATENT DOCUMENTS 5,534,474 A     7/1996    Becker et al. ............... 502/152
5,589,555 A    12/1996    Zboril et al. .................. 526/64

FOREIGN PATENT DOCUMENTS

EP        0 668 295 A1    8/1995

OTHER PUBLICATIONS

Martyn P. Coles and Richard F. Jordan, Cationic Aluminum Alkyl Complexes Incorporating Amidinate Ligands. Transition–Metal–Free Ethylene Polymerization Catalysts, J.Am. Chem. Soc. 1997, 119, 8125–8126.

Michael Burce, Vernon C. Gibson, Carl Redshaw, Gregory A. Solan, Andrew J.P. White and David J. Williams, Aluminum ethylene polymerization catalysts based on monoanionic N,N,N–pyridylimino–amide ligands, Chem. Commun., 1998, 2523–2524.

*Primary Examiner*—Porfirio Nazario-Gonzalez
(74) *Attorney, Agent, or Firm*—Kenneth H. Johnson

(57) ABSTRACT

It is known to polymerize olefins using transition metal complexes and/or compounds. There is an ongoing search for catalysts for olefin polymerization which do not rely on transition metals as the active center. The present invention provides novel aluminum phosphinimine complexes which are useful in the polymerization of olefins.

4 Claims, No Drawings

ALUMINUM COMPLEXES FOR OLEFIN POLYMERIZATION

This is a division of application Ser. No. 09/375,618, filed Aug. 17, 1999, now U.S. Pat. No. 6,235,919 B1.

FIELD OF THE INVENTION

The present invention relates to novel aluminum complexes. The complexes are of aluminum and a bridged phosphinimine compound. The complexes may have one aluminum atom or may be a "dimer" having two aluminum atoms.

BACKGROUND OF THE INVENTION

Over the last fifteen years or so there has been an increasing interest in complexes other than the Ziegler-Natta complexes which have the potential to polymerize olefins. The work of EXXON and Dow have lead to the commercialization of metallocene and constrained geometry catalysts which produce polymers tending to have a single active catalyst site. This type of research has lead to more complex ligand structures such as those of Brookhart which also show activity as polymerization catalysts. These systems are used with transition metals as the active catalyst center. There is a desire to find new species which may be capable of olefin polymerization with metals other than the transition metals.

There was a poster presentation by Christopher M. Ong and Professor Douglas W. Stephan of the University of Windsor at the summer meeting of the Chemical Institute of Canada in Toronto which disclosed aluminum phosphinimine complexes. The complex disclosed is a mono aluminum complex having phenyl substituents on the phosphorus atom and trimethyl silyl substituents on the nitrogen atom. The presentation does not disclose the dimer of the present invention.

Jordan et al. JACS 1997, 119, 8125 "Cationic Aluminum Alkyl Complexes Incorporating Amidinate Ligands", teaches amine, imine and aluminum complexes. The paper does not teach complexes of aluminum phosphinimine. The polymerization activity of the complexes of Jordan is very low.

Gibson et al. Chem. Commun. 1998, 2523 "Novel Aluminum Ethylene Polymerization Catalysts Based on Monoaonic N,N,N,-Pyridyliminoamide Ligands" teaches the polymerization of ethylene using a complex with a "Brookhart" tridentate ligand and aluminum. Gibson's catalyst does not teach the complexes of aluminum phosphinimine of the present invention. Further, the polymerization activity of the complexes of Gibson is very low.

The present invention seeks to provide novel aluminum complexes and processes for polymerizing olefins using such complexes.

SUMMARY OF THE INVENTION

The present invention provides a process for preparing a complex of aluminum and a bridged phosphinimine comprising reacting moles of a bridged phosphinimine compound of the formula I:

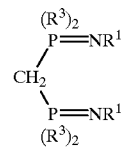

wherein each $R^1$ is independently selected from the group consisting of $C_{1-8}$ straight or branched alkyl radical or a $C_{6-12}$ cyclic aliphatic or aromatic radical; radicals of the formula $Si(R^4)_3$ wherein each $R^4$ is independently selected from the group consisting of $C_{1-8}$ alkyl and alkoxy radicals; and $R^3$ is selected from the group consisting of $C_{1-8}$ alkyl radicals and $C_{6-12}$ aromatic radicals which are unsubstituted or substituted with one or more halogen atoms or a $C_{1-4}$ alkyl radical with an aluminum compound of the formula III $(Al(R^2)_{3-n}X_n)$ wherein each $R^2$ is independently selected from the group consisting of $C_{1-8}$ alkyl radicals, X is a halogen atom and n is 0, 1, or 2 under an inert atmosphere, in an inert hydrocarbyl solvent or diluent at a temperature from 50° C. to 200° C. provided that if the molar ratio of compound of formula I to aluminum compound is from 0.8 to 1.20, $R^3$ can not be phenyl if $R^1$ is trimethyl silyl, X is chlorine and n is 2.

The present invention also provides a complex of formula IV:

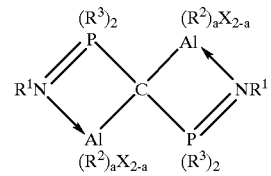

wherein each $R^1$ is independently selected from the group consisting of $C_{1-8}$ straight or branched alkyl radical or a $C_{6-12}$ cyclic aliphatic or aromatic radical; radicals of the formula $Si(R^4)_3$ wherein each $R^4$ is independently selected from the group consisting of $C_{1-8}$ alkyl and alkoxy radicals; $R^2$ is independently selected from the group consisting of $C_{1-8}$ alkyl radicals, X is a halogen atom and a is 1 or 2; and $R^3$ is selected from the group consisting of $C_{1-8}$ alkyl radicals and $C_{6-12}$ aromatic radicals which are unsubstituted or substituted with one or more halogen atoms or a $C_{1-4}$ alkyl radical.

The present invention further provides a complex of the formula V:

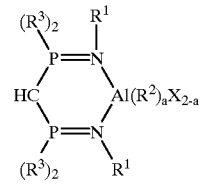

wherein each $R^1$ is independently selected from the group consisting of $C_{1-8}$ straight or branched alkyl radical or a $C_{6-12}$ cyclic aliphatic or aromatic radical; radicals of the formula $Si(R^4)_3$ wherein each $R^4$ is independently selected from the group consisting of $C_{1-8}$ alkyl and alkoxy radicals; $R^2$ is independently selected from the group consisting of $C_{1-8}$ alkyl radicals, X is a halogen atom and a is 1 or 2; and $R^3$ is selected from the group consisting of $C_{1-8}$ alkyl radicals and $C_{6-12}$ aromatic radicals which are unsubstituted or substituted with one or more halogen atoms or a $C_{1-4}$ alkyl radical provided that $R^3$ can not be phenyl if $R^1$ is trimethyl silyl, X is chlorine and n is 2.

The present invention further provides a process for the polymerization of alpha olefins at a temperature from 20° C. to 250° C. and at a pressure from 15 to 4500 psig in the presence of the complexes of formula IV and an activator selected from the group consisting of:

(i) aluminoxane compounds $R^{20}{}_2AlO(R^{20}AlO)_mAlR^{20}{}_2$ wherein each $R^{20}$ is independently selected from the group consisting of $C_{1-20}$ hydrocarbyl radical and m is from 5 to 30 to provide a molar ratio of aluminum in the activator to aluminum in the complex from 20:1 to 1000:1;

(ii) anions of the formula $[B(R^{18})_4]^-$ wherein each $R^{18}$ is independently selected from the group consisting of phenyl radicals which are unsubstituted or substituted by up to 5 substituents selected from the group consisting of a fluorine atom, a $C_{1-4}$ alkyl or alkoxy radical which is unsubstituted or substituted by a fluorine atom and a silyl radical of the formula $-Si(R^{19})_3$; wherein each $R^{19}$ is independently selected from the group consisting of a hydrogen atom and a $C_{1-4}$ alkyl radical; and an activator of the formula $[B(R^{18})_3]$ wherein $R^{18}$ is as defined above, to provide a molar ratio of B:Al from 0.4 to 1.2; and (iii) a mixture of (i) and (ii) above.

The present invention further provides a process for polymerizing one or more $C_{2-8}$ olefins at a temperature from 20° C. to 120° C. and at a pressure from 15 to 4500 psig in the presence of a complex of the formula V:

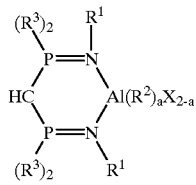

wherein each $R^1$ is independently selected from the group consisting of $C_{1-8}$ straight or branched alkyl radical or a $C_{6-12}$ cyclic aliphatic or aromatic radical; radicals of the formula $Si(R^4)_3$ wherein each $R^4$ is independently selected from the group consisting of $C_{1-8}$ alkyl and alkoxy radicals; $R^2$ is independently selected from the group consisting of $C_{1-8}$ alkyl radicals, X is a halogen atom and a is 1 or 2; and $R^3$ is selected from the group consisting of $C_{1-8}$ alkyl radicals and $C_{6-12}$ aromatic radicals which are unsubstituted or substituted with one or more halogen atoms or a $C_{1-4}$ alkyl radical and an activator selected from the group consisting of:

(i) aluminoxane compounds $R^{20}{}_2AlO(R^{20}AlO)_mAlR^{20}{}_2$ wherein each $R^{20}$ is independently selected from the group consisting of $C_{1-20}$ hydrocarbyl radical and m is from 5 to 30 to provide a molar ratio of aluminum in the activator to aluminum in the complex from 20:1 to 1000:1;

(ii) anions of the formula $[B(R^{18})_4]^-$ wherein each $R^{18}$ is independently selected from the group consisting of phenyl radicals which are unsubstituted or substituted by up to 5 substituents selected from the group consisting of a fluorine atom, a $C_{1-4}$ alkyl or alkoxy radical which is unsubstituted or substituted by a fluorine atom and a silyl radical of the formula $-Si(R^{19})_3$; wherein each $R^{19}$ is independently selected from the group consisting of a hydrogen atom and a $C_{1-4}$ alkyl radical; and an activator of the formula $[B(R^{18})_3]$ wherein $R^{18}$ is as defined above, to provide a molar ratio of B:Al from 0.8 to 1.2; and (iii) a mixture of (i) and (ii) above.

DETAILED DESCRIPTION OF THE PREFERRED EMBODIMENTS

The term "scavenger" as used in this specification is meant to include those compounds effective for removing polar impurities from the reaction solvent. Such impurities can be inadvertently introduced with any of the polymerization reaction components, particularly with solvent, monomer and catalyst feed; and can adversely affect catalyst activity and stability. It can result in decreasing or even elimination of catalytic activity, particularly when an activator capable of ionizing the catalyst is also present.

In the complexes of the present invention each $R^1$ may be independently selected from the group consisting of $C_{1-8}$ straight or branched alkyl radical or a $C_{6-12}$ cyclic aliphatic or aromatic radical; and radicals of the formula $Si(R^4)_3$ wherein each $R^4$ is independently selected from the group consisting of $C_{1-8}$ alkyl and alkoxy radicals.

If $R^1$ is a hydrocarbyl radical it may be selected from the group consisting of a $C_{1-4}$ straight or branched alkyl radical or a $C_{6-12}$ cyclic aliphatic or aromatic radical. Suitable hydrocarbyl radicals include methyl, ethyl, propyl, butyl, iso-butyl, tert-butyl and phenyl radicals.

In the complexes of formula V, $R^1$ may be a silyl radical of the formula $Si(R^4)_3$ wherein each $R^4$ is independently selected from the group consisting of $C_{1-8}$ alkyl and alkoxy radicals, preferably $R^4$ is selected from the group consisting of $C_{1-4}$ alkyl radicals. It should be noted that when $R^4$ is methyl, $R^3$ can not be phenyl, X can not be chlorine and n can not be 2.

In the complexes of the present invention $R^3$ may be selected from the group consisting of consisting of $C_{1-8}$ alkyl radicals and $C_{6-12}$ aromatic radicals which are unsubstituted or substituted with one or more halogen atoms or a $C_{1-4}$ alkyl radical. Suitable radicals include $C_{1-4}$ straight chained or branched alkyl radicals and $C_{6-12}$ cyclic aliphatic or aromatic radicals. These radicals include methyl, ethyl, propyl, butyl, iso-butyl, tert- butyl, and phenyl radicals.

In some embodiments of the present invention the $R^1$ substituents are the same. In some embodiments of the present invention the $R^3$ substituents are the same.

The bridged phosphinimine compound of formula I above may be reacted with an aluminum compound of formula III $(Al(R^2)_{3-n}X_n)$ wherein each $R^2$ is independently selected from the group consisting of $C_{1-8}$ alkyl and alkoxy radicals, X is a halogen atom and n is 0, 1, or 2. In some embodiments of the present invention $R^2$ may be selected from the group consisting of $C_{1-4}$ alkyl radicals. Suitable halogen atoms include chlorine atoms.

If the bridged phosphinimine compound of formula I is reacted with from about 0.8 to about 1.2, preferably from about 0.95 to about 1.05 moles of the aluminum compound of formula III per mole of phosphinimine; a compound of formula V:

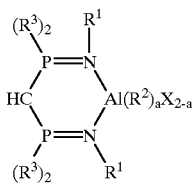

wherein $R^1$ and $R^3$ are as defined above, is obtained.

The bridged phosphinimine compound of formula I above may be reacted with an aluminum compound of formula III $(Al(R^2)_{3-n}X_n)$ wherein each $R^2$ is independently selected from the group consisting of a $C_{1-8}$ alkyl radical, X is a halogen atom and n is 0 or 1. In some embodiments of the present invention $R^2$ may be selected from the group consisting of $C_{1-4}$ alkyl radicals. Suitable halogen atoms include chlorine atoms.

If the bridged phosphinimine compound of formula I is reacted with from about 1.8 to about 2.2, preferably from about 1.95 to about 2.05 moles of the aluminum compound of formula III per mole of phosphinimine; a compound of formula IV:

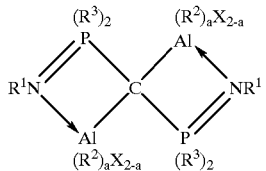

wherein $R^1$, $R^2$ and $R^3$ are as defined above, is obtained.

The reaction is conducted under an inert atmosphere, such as argon, in an inert solvent or diluent such as a hydrocarbyl solvent or diluent at temperature from about 50° C. to 200° C., preferably from about 120° C. to 180° C.

The resulting compounds of either formula V or IV may then be used to polymerize one or more olefins, generally alpha olefins, typically having from 2 to 10, preferably 8 carbon atoms or less. Illustrative non-limiting examples of such alpha-olefins are one or more of propylene, 1-butene, 1-pentene, 1-hexene, 1-octene and 1-decene.

The compound and an activator are dissolved or suspended in an inert solvent or diluent such as a hydrocarbyl solvent or diluent in the presence of an activator and the ethylene is introduced into the reaction vessel.

The polymerization may be conducted at temperatures from about 20 to about 250° C. Depending on the product being made, this temperature may be relatively low such as from 20° C. to about 120° C. (desirably 119° C. or less) for a slurry polymerization or from about 120° C. to 250° C. for a solution polymerization. The pressure of the reaction may be as high as about 15,000 psig (103.5 MPa gauge) (for the older high pressure processes) or may range from about 15 to 4,500 psig (0.1035 MPa gauge to about 31.01 MPa gauge).

Solution polymerization processes are fairly well known in the art. These processes are conducted in the presence of an inert hydrocarbon solvent typically a $C_{5-12}$ hydrocarbon which may be unsubstituted or substituted by $C_{1-4}$ alkyl group such as pentane, hexane, heptane, octane, cyclohexane, methylcyclohexane or hydrogenated naphtha. An additional solvent is Isopar E ($C_{8-12}$ aliphatic solvent, Exxon Chemical Co.).

The polyethylene polymers which may be prepared in accordance with the present invention typically comprise not less than 60, preferably not less than 70, most preferably not less than 80 weight % of ethylene and the balance of one or more $C_{4-10}$ alpha olefins, preferably selected from the group consisting of 1-butene, 1-hexene and 1-octene.

The activator may be selected from the group consisting of:
(i) an aluminoxane; and
(ii) an activator capable of ionizing the catalyst (which may be used in combination with an alkylating activator).

The aluminoxane activator may be of the formula $(R^{20})_2AlO(R^{20}AlO)_mAl(R^{20})_2$ wherein each $R^{20}$ is independently selected from the group consisting of $C_{1-20}$ hydrocarbyl radicals, m is from 0 to 50, and preferably $R^{20}$ is a $C_{1-4}$ alkyl radical and m is from 5 to 30. The aluminoxane activator may be used prior to the reaction but preferably in situ alkylation is typical (e.g. alkyl groups replacing leaving ligands, hydrogen or halide groups).

Activation with aluminoxane generally requires a molar ratio of aluminum in the activator to the catalyst from 20:1 to 1000:1.

The activator of the present invention may be a combination of an alkylating activator which also serves as a scavenger other than aluminoxane in combination with an activator capable of ionizing the catalyst.

The alkylating activator (which may also serve as a scavenger) may be selected from the group consisting of: $(R)_pMgX_{2-p}$ wherein X is a halide, each R is independently selected from the group consisting of $C_{1-10}$ alkyl radicals, preferably $C_{1-8}$ alkyl radicals and p is 1 or 2; $(R)_qZnX_{2-q}$ wherein R is as defined above, X is halogen and q is 1 or 2; $(R)_sAlX_{3-s}$ wherein R is as defined above, X is halogen and s is an integer from 1 to 3. Preferably, in the above compounds R is a $C_{1-4}$ alkyl radical and X is chlorine. Commercially available compounds include triethyl aluminum (TEAL), diethyl aluminum chloride (DEAC), dibutyl magnesium $((Bu)_2Mg)$ and butyl ethyl magnesium (BuMgEt).

The activator capable of ionizing the catalyst may be selected from the group consisting of:
(i) compounds of the formula $[R^{15}]^+[B(R^{18})_4]^-$ wherein B is a boron atom, $R^{15}$ is a cyclic $C_{6-7}$ aromatic cation or a triphenyl methyl cation and each $R^{18}$ is independently selected from the group consisting of phenyl radicals which are unsubstituted or substituted with from 3 to 5 substituents selected from the group consisting of a fluorine atom, a $C_{1-4}$ alkyl or alkoxy radical which is unsubstituted or substituted by a fluorine atom, and a silyl radical of the formula —Si—$(R^{19})_3$ wherein each $R^{19}$ is independently selected from the group consisting of a hydrogen atom and a $C_{1-4}$ alkyl radical; and
(ii) compounds of the formula $[(R^{16})_tZH]^+[B(R^{18})_4]^-$ wherein B is a boron atom, H is a hydrogen atom, Z is a nitrogen atom or phosphorus atom, t is 3 and $R^{16}$ is selected from the group consisting of $C_{1-8}$ alkyl radicals, a phenyl radical which is unsubstituted or substituted by up to three $C_{1-4}$ alkyl radicals, or one $R^{16}$ taken together with the nitrogen atom to form an anilinium radical and $R^{18}$ is as defined above; and
(iii) compounds (activators) of the formula $B(R^{18})_3$ wherein $R^{18}$ is as defined above.

In the above compounds, preferably $R^{18}$ is a pentafluorophenyl radical, $R^{15}$ is a triphenylmethyl cation, Z is a nitrogen atom and $R^{16}$ is a $C_{1-4}$ alkyl radical or $R^{16}$ taken together with the nitrogen atom to form an anilinium radical which is substituted by two $C_{1-4}$ alkyl radicals.

The activator capable of ionizing the catalyst abstracts one or more $R^2$ substituents so as to ionize the catalyst center into a cation, but not to covalently bond with the catalyst; and to provide sufficient distance between the ionized catalyst and the ionizing activator to permit a polymerizable olefin to enter the resulting active site. Examples of compounds capable of ionizing the catalyst include the following compounds:

triethylammonium tetra(phenyl)boron,
tripropylammonium tetra(phenyl)boron,
tri(n-butyl)ammonium tetra(phenyl)boron,
trimethylammonium tetra(p-tolyl)boron,
trimethylammonium tetra(o-tolyl)boron,
tributylammonium tetra(pentafluorophenyl)boron,
tributylammonium tetra(pentafluorophenyl)boron,
tri(n-butyl)ammonium tetra(o-tolyl)boron,
N,N-dimethylanilinium tetra(phenyl)boron,
N,N-diethylanilinium tetra(phenyl)boron,
N,N-diethylanilinium tri(phenyl)n-butylboron,
N,N-2,4,6-pentamethylanilinium tetra(phenyl)boron,
di-(isopropyl)ammonium tetra(pentafluorophenyl)boron,
dicyclohexylammonium tetra(phenyl)boron,
triphenylphosphonium tetra(phenyl)boron,
tri(methylphenyl)phosphonium tetra(phenyl)boron,
tri(dimethylphenyl)phosphonium tetra(phenyl)boron,
tropillium tetrakispentafluorophenyl borate,
triphenylmethylium tetrakispentafluorophenyl borate,
benzene (diazonium) tetrakispentafluorophenyl borate,
tropillium phenyltrispentafluorophenyl borate,
triphenylmethylium phenyltrispentafluorophenyl borate,
benzene (diazonium) phenyltrispentafluorophenyl borate,
tropillium tetrakis (2,3,5,6-tetrafluorophenyl) borate,
triphenylmethylium tetrakis (2,3,5,6-tetrafluorophenyl) borate,
benzene (diazonium) tetrakis (3,4,5-trifluorophenyl) borate,
tropillium tetrakis (3,4,5-trifluorophenyl) borate,
benzene (diazonium) tetrakis (3,4,5-trifluorophenyl) borate,
tropillium tetrakis (1,2,2-trifluoroethenyl) borate,
triphenylmethylium tetrakis (1,2,2-trifluoroethenyl) borate,
benzene (diazonium) tetrakis (1,2,2-trifluoroethenyl) borate,
tropillium tetrakis (2,3,4,5-tetrafluorophenyl) borate,
triphenylmethylium tetrakis (2,3,4,5-tetrafluorophenyl) borate, and
benzene (diazonium) tetrakis (2,3,4,5-tetrafluorophenyl) borate.

Readily commercially available activators which are capable of ionizing the catalyst include:
N,N-dimethylaniliniumtetrakispentafluorophenyl borate,
triphenylmethylium tetrakispentafluorophenyl borate, and
trispentafluorophenyl boron.

If the catalyst is a mono aluminum compound (e.g., of formula V) and the activator is ionic (i.e., a boron compound) the molar ratio of boron in the activator to aluminum in the complex may be from about 0.8 to about 1.2, preferably from about 0.9 to 1.1. If the aluminum compound contains two aluminum atoms (e.g. the "dimer") the molar ratio of boron in the activator to aluminum in the complex may be from about 0.4 to about 1.2, preferably from about 0.5 to 1.1.

If the aluminum compound of formula IV or V is activated with a combination of an aluminum alkyl compound (which may include aluminoxane), and a compound capable of ionizing the catalyst; the molar ratios of aluminum in the compound of formula IV or V:metal in the alkylating agent (e.g. Al):metalloid (e.g. boron or phosphorus) in the activator capable of ionizing the catalyst (e.g. boron) may range from 1:1:1 to 1:100:5 for the complexes of formula V and from 1:1:0.4 to 1:100:5 for complexes of formula IV.

Preferably, the alkylating activator is premixed/reacted with the catalyst and the resulting alkylated species is then reacted with the activator capable of ionizing the catalyst.

It is believed the complexes of the present invention may be used in the presence of a support. An exemplary list of support materials include metal oxides (such as silica, alumina, silica-alumina, titania and zirconia); metal chlorides (such as magnesium chloride); talc, polymers (including polyolefins); partially prepolymerized mixtures of a group 4 metal complex, activator and polymer; spray dried mixtures of the group 4 metal complex, activator and fine "inert" particles (as disclosed, for example, in European Patent Office Application 668,295 (to Union Carbide)).

A typical support material is silica. The silica may be pre-treated with an aluminoxane (especially methylaluminoxane or "MAO") prior to the deposition of the aluminum complex. The procedure for preparing "supported MAO" which is described in U.S. Pat. No. 5,534,474 (to Witco) is preferred for reasons of economy. It will be recognized by those skilled in the art that silica may be characterized by such parameters as particle size, pore volume and residual silanol concentration. The pore size and silanol concentration may be altered by heat treatment or calcining. The residual silanol groups provide a potential reaction site between the aluminoxane and the silica (and, indeed, some off gassing is observed when aluminoxane is reacted with silica having residual silanol groups). This reaction may help to "anchor" the aluminoxane to the silica (which, in turn, may help to reduce reactor fouling).

The particle size, pore volume and residual silanol concentration may be influenced by reactor conditions. Typical silicas are dry powders having a particle size from 1 to 200 microns (with an average particle size from 30 to 100 being especially suitable); pore size from 50 to 500 Angstroms; and pore volumes of from 0.5 to 5.0 cubic centimeters per gram. As a general guideline, the use of commercially available silicas, such as those sold by W. R. Grace under the trademarks Davison 948 or Davison 955, are suitable.

In a solution polymerization, the monomers are dissolved/dispersed in the solvent either prior to being fed to the reactor or for gaseous monomers, the monomer may be fed to the reactor so that it will dissolve in the reaction mixture. Prior to mixing, the solvent and monomers are generally purified to remove polar moieties. The polar moieties or catalyst poisons include water, oxygen, metal impurities, etc. Preferably steps are taken before provision of such into the reaction vessel, for example by chemical treatment or careful separation techniques after or during the synthesis or preparation of the various components. The feedstock purification prior to introduction into the reaction solvent follows standard practices in the art (e.g. molecular sieves, alumina beds and oxygen removal catalysts) are used for the purification of ethylene, alpha-olefin and optional diene. The solvent itself as well (e.g. cyclohexane and toluene) is similarly treated. In some instances, out of an abundance of caution, excess scavenging activators may be used in the polymerization process.

The feedstock may be heated prior to feeding into the reactor. However, in many instances it is desired to remove heat from the reactor so the feedstock may be at ambient temperature to help cool the reactor.

Generally, the components may be premixed in the solvent for the reaction or fed as separate streams to the reactor. In some instances, premixing is desirable to provide a reaction time for the catalyst components prior to entering the reaction. Such an "in line mixing" technique is described in a number of patents in the name of DuPont Canada Inc. For example, it is described in U.S. Pat. No. 5,589,555 issued Dec. 31, 1996.

The reactor may comprise a tube or serpentine reactor used in "high pressure" polymerizations or it may comprise one or more reactors or autoclaves. It is well known that the use in series of two such reactors each of which may be operated so as to achieve different polymer molecular weight characteristics. The residence time in the reactor system will depend on the design and the capacity of the reactor. Generally, the reactors should be operated under conditions to achieve a thorough mixing of the reactants. On leaving the reactor system, the solvent is removed and the resulting polymer is finished in a conventional manner.

The present invention will be illustrated by the following non-limiting examples in which, unless otherwise specified, part means parts by weight (e.g. grams) and per cent means weight per cent.

Synthesis of Aluminum Complexes

Preparation of $[AlMe_2\{HC(Ph_2P=NSiMe_3)_{2-\kappa}{}^2N,N'\}]$ (KA-27)

To a toluene (5 mL) solution of $H_2C(Ph_2P=NSiMe_3)_2$ (0.20 g, 0.36 mmol), AlMe3 (2.0 M solution in toluene, 0.18 mL, 0.36 mmol) was added with stirring at room temperature. Immediately evolution of gas was observed. The reaction mixture was stirred at room temperature for a day. Colorless crystals were obtained upon concentration to half of the original volume and leaving the flask at room temperature for three days. The product was filtered and dried under vacuum. Yield=0.15 g, 68.2%. IR data (Nujol Mull): 1438 s, 1254 s, 1197 m, 1175 m, 1159 w, 1149 m, 1112 s, 1039 s, 1026 s, 1007 m, 1000 m, 963 w, 942 w, 906 m, 846 s, 776 s, 737 s, 726 s, 692 s, 670 s, 638 w, 628 w, 616 w, 552 m, 532 m, 518 m. $^1H$ NMR ($C_6D_6$): δ7.70 (m, phenyl), 6.95 (m, phenyl), 1.90 (s, P—CH—P), 0.18 (s, $CH_3Si$ methyl), −0.49 (s, $CH_3$—Al), $^{13}C$ $\{^1H\}$NMR ($C_6D_6$): δ135.6 (m, ipso phenyl), 132.2 (t,$^2J_{PC}$=5.3 Hz, ortho phenyl), 130.6 (s, para phenyl), 128.1 (t,$^3J_{PC}$=6.1 Hz, meta phenyl), 25.2 (t, P—CH—P, $^1J_{PC}$=113.9 Hz), 4.6 (s, $CH_3Si$), 2.4 (s, $CH_3$—Al). $^{31}P\{^1H\}$NMR ($C_6D_6$): δ29.5 (s). Analysis calculated for $C_{33}H_{45}AlN_2P_2Si_2$: C, 64.47; H, 7.38; N, 4.56. Found: C, 64.23; H, 7.69; N, 4.49.

Preparation of $[(AlMe_2)\{\mu_2\text{—}C(Ph_2P=NSiMe_3)_{2-\kappa}{}^4C,C'N, N'\}]$ (KA-108)

To a toluene (5 mL) solution of $H_2C(Ph_2P=NSiMe_3)_2$ (0.20 g, 0.36 mmol), AlMe3 (2.0 M solution in toluene, 0.36 mL, 0.72 mmol) was added with stirring at room temperature. Immediately evolution of gas was observed. The reaction mixture was stirred at room temperature for a day and refluxed for 3 hours. Colorless crystals were obtained upon concentration to half of the original volume and leaving the flask at room temperature for two days. The product was filtered and dried under vacuum. Yield=0.16 g, 66.6%. IR data (Nujol Mull): 1485 w, 1437 s, 1251 s, 1187 m, 1119 s, 1119 s,1109 s, 1090 s,1050 s, 999 w, 850 s, 835 s, 780 s, 756 w, 743 m, 736 s, 721 s, 694 s, 670 s, 651 m, 635 m, 593 m, 549 s, 513 m, 467 m, 414 m. $^1H$ NMR ($C_6D_6$): δ7.70 (m, phenyl), 7.35 (m, phenyl), 7.10 (m, toluene), 6.90 (m, toluene), 6.65 (m, phenyl), 2.10 (s, toluene), 0.27 (s, $CH_3$—Al), 0.11 (s, $CH_3Si$), −0.75 (s, $CH_3$—Al). $^{13}C\{^1H\}$NMR ($C_6D_6$): 137.0 (m, ipso phenyl), 132.7 (m, ortho phenyl), 131.4 (s, ortho phenyl), 131.0 (s, meta phenyl), 129.9 (m, ipso phenyl), 129.3 (s, para phenyl), 128.8 (s, meta phenyl), 125.6 (s, para phenyl), 2.3 (s, $CH_3Si$), −2.5 (s, $CH_3$—Al), −4.1 (s, $CH_3$—Al). $^{31}P\{^1H\}$NMR ($C_6D_6$): δ27.6 (s). Analysis calculated for $C_{35}H_{50}Al_2N_2P_2Si_2$: C, 62.66; H, 7.51; N, 4.18. Found: C, 62.98; H, 7.72; N, 3.99.

Preparation of $[AlEt(Cl)\{HC(Ph_2P=NSiMe_3)_{2-\kappa}{}^2N,N'\}]$ (KA-13)

To a toluene (5 mL) solution of $AlEt_2Cl$ (1.8 M solution in toluene, 0.20 mL, 0.36 mmol) was added $H_2C(Ph_2P=NSiMe_3)_2$ (0.20 g, 0.36 mmol) with stirring at room temperature. Immediately evolution of gas was observed. The reaction mixture was stirred at room temperature for 12 hours. Colorless crystals were obtained upon concentration to half of the original volume and leaving the flask at room temperature for three days. The product was filtered and dried under vacuum. Yield=0.18 g, 77.5%. IR data (Nujol Mull): 1482 m, 1437 s, 1310 w, 1263 m, 1255 m, 1248 s,1192 s, 1113 s, 1040 s, 1026 s, 1000 s, 845 s, 804 s, 783 s, 763 m, 732 s, 697 m, 639 m, 609 m, 597 m, 554 m, 530 m, 510 m. $^1H$ NMR ($C_6D_6$): δ7.81 (m, phenyl), 7.39 (m, phenyl), 7.00 (m, phenyl), 6.81 (m, phenyl), 1.78 (t, P—CH—P, $^2J_{PH}$=4.5 Hz), 1.75 (t, At-Et ($CH_3$)), 0.93 (q, At-Et ($CH_2$)), 0.35 (s, $CH_3Si$ methyl). $^{13}C$ $\{^1H\}$NMR ($C_6D_6$): δ135.1 (m, ipso phenyl), 131.8 (m, ortho phenyl), 130.2 (s, meta phenyl), 128.2 (m, para phenyl), 25.4 (t, P—CH—P, $^1J_{PC}$=118.0 Hz), 11.1 (s, Et($CH_3$)—Al), 4.8 (s, $CH_3Si$). $^{31}P\{^1H\}$NMR ($C_6D_6$): δ28.9 (s). Analysis calculated for $C_{33}H_{44}AlClN_2P_2Si_2$: C, 61.05; H, 6.83; N, 4.32. Found: C, 60.82; H, 6.69; N, 4.23.

Preparation of $[(Al(^iBu)_2\{\mu_2\text{—}C(Ph_2P=NSiMe_3)_{2-\kappa}{}^4C,C'N, N'\}]$ (KB-139)

To a toluene (10 mL) solution of $H_2C(Ph_2P=NSiMe_3)_2$ (1.00 g, 1.79 mmol) was added TIBAL (Trisisobutylaluminum) solution (1.07 M solution in toluene, 3.7 mL, 3.95 mmol) with stirring. Gas evolution was observed. The reaction mixture was heated at 130° C. for 15 hours. Solvent was evaporated under vacuum and the residue was mixed with hexane (5 mL) and cooled at −15° C. Micro-crystalline solid deposited in a day was collected and washed with 4 mL of cold hexane to give ~800 mg of the product. Another ~220 mg of the product was isolated from the combined mother solutions upon concentration and cooling. Yield=1.02 g, 67.9%.

Polymerization Results

In the examples, the pressures given are gauge pressures. The following abbreviations and terms are used:

Branching: reported as the number of methyl groups per 1000 methylene groups in the polymer. It is determined by FT-IR.

Polydispersity (Pd): weight average molecular weight (Mw) divided by number average molecular weight (Mn).

DSC: differential scanning calorimetry.

GPC: gel permeation chromatography.

MeOH: methanol.

PMAO-IP: a type of polymethylaluminoxane.

m.p.: polymer melting point.

All the polymerization experiments described below were conducted using a 500 mL Autoclave Engineers Zipperclave reactor. All the chemicals (solvent, catalyst and cocatalyst) were fed into the reactor batchwise except ethylene which was fed on demand. No product was removed during the polymerization reaction. As are known to those skilled in the art, all the feed streams were purified prior to feeding into the reactor by contact with various absorption media to remove catalysts killing impurities such as water, oxygen, sulfur and polar materials. All components were stored and manipulated under an atmosphere of purified argon or nitrogen. The reactor uses a programmable logic control (PLC) system with Wonderware 5.1 software for the process control. Ethylene polymerizations were performed in the reactor equipped with an air driven stirrer and an automatic temperature control system.

Polymerization temperature was 50° C. for slurry polymerizations and 160° C. for solution polymerizations. The polymerization reaction time varied from 4 to 40 minutes for each experiment. The reaction was terminated by adding 5 mL of methanol to the reactor and the polymer was recovered by evaporation of the toluene or by drying it in vacuum. The polymerization activities were calculated based on the weight of the polymer produced.

Anhydrous toluene was purchased from Aldrich and purified over a series of purification beds (various absorption media) to remove the impurities. 1-octene was purchased from Aldrich and purified over a series of purification beds (various absorption media) to remove the impurities. $[CPh_3][B(C_6F_5)_4]$ was purchased from Asahi Glass Inc.; lot #: 980224. PMIP was purchased from Akzo Nobel and contains 13.9 weight % aluminum. Ethylene was purchased form Praxair in polymer grade.

Polymer molecular weights and molecular weight distributions were measured by GPC (Waters 150-C) at 140° C. in 1,2,4-trichlorobenzene calibrated using polyethylene standards.

DSC was conducted on a DSC 220 C from Seiko Instruments. The heating rate is 10° C./min from 0 to 200° C.

FT-IR was conducted on a Nicolet Model 750 Magna IR spectrometer.

Slurry Polymerization Experiments

TABLE 1

Polymerization Data[1]

| Catalyst/Cocatalyst | Average Run Temperature (° C.) | Run Time (min.) | Polymerization Activity (g polymer/ mmol Al*hr) |
| --- | --- | --- | --- |
| KA-108/$[CPh_3][B(C_6F_5)_4]$[2] | 120.4 | 4 | 2886.8 |
| KA-108/$[CPh_3][B(C_6F_5)_4]$[3] | 50.5 | 20 | 8.1 |
| KA-27/$[CPh_3][B(C_6F_5)_4]$[2] | 53.8 | 40 | 3.5 |
| KA-13/PMAO-IP[4] | 56.3 | 30 | 15.5 |
| KA-13/PMAO-IP//$[CPh_3][B(C_6F_5)_4]$[5] | 54.8 | 30 | 68.1 |
| KB-139//$[CPh_3][B(C_6F_5)_4]$[6] | 53.8 | 35 | 378.4 |

[1]General homopolymerization conditions: 50° C. as a setting temperature; 300 psig of C2; 300 µmol/L of catalyst concentration; 216 mL of toluene as solvent.
[2]Trityl borate activation: trityl borate as a cocatalyst at 315 µmol/L and PMAO-IP at 1 mmol/L as a scavenger.
[3]Copolymerization conditions: 100 psig of C2; 30 mL of 1-octene; trityl borate activation, the rest conditions as in No. 2.
[4]PMAO-IP activation at Al/Al = 60.
[5]In-situ alkylation plus trityl borate activation: 50° C. as a setting temperature PMAO-IP as an alkylation reagent with Al/Al = 20; trityl borate as cocatalyst at B/Al = 1.05; PMAO-IP at 1 mmol/L as a scavenger.
[6]Trityl borate activation at 630 µmol/L, the rest conditions as in general polymerization conditions.

TABLE 2

Polymer Property Data

| Catalyst/Cocatalyst | Mw(*10$^{-3}$) | Pd | m.p. |
| --- | --- | --- | --- |
| KA-108/$[CPh_3][B(C_6F_5)_4]$[2] | 721.9 | 3.7 | 135.2 |
| KA-108/$[CPh_3][B(C_6F_5)_4]$[3] | 840.1 | 1.7 | 105.0 |
| KA-27/$[CPh_3][B(C_6F_5)_4]$[2] | 1252.0 | 1.8 | 142.3 |
| KA-13/PMAO-IP[4] | 1255.0 | 2.4 | 137.9 |
| KA-13/PMAO-IP//$[CPh_3][B(C_6F_5)_4]$[5] | 1397.0 | 2.0 | 141.1 |
| KB-139//$[CPh_3][B(C_6F_5)_4]$[6] | 1526.0 | 1.6 | 134.3 |

[1]General homopolymerization conditions: 50° C. as a setting temperature; 300 psig of C2; 300 µmol/L of catalyst concentration; 216 mL of toluene as solvent.
[2]Trityl borate activation: trityl borate as a cocatalyst at 315 µmol/L and PMAO-IP at 1 mmol/L as a scavenger.
[3]Copolymerization conditions: 100 psig of C2; 30 mL of 1-octene; trityl borate activation, the rest conditions as in No. 2.
[4]PMAO-IP activation at Al/Al = 60.
[5]In-situ alkylation plus trityl borate activation: 50° C. as a setting temperature PMAO-IP as an alkylation reagent with Al/Al = 20; trityl borate as cocatalyst at B/Al = 1.05; PMAO-IP at 1 mmol/L as a scavenger.
[6]Trityl borate activation at 630 µmol/L, the rest conditions as in general polymerization conditions.

Solution Polymerization Experiments

TABLE 3

Polymerization Data[1]

| Catalyst/Cocatalyst | Average Run Temperature (° C.) | Run Time (min.) | Polymerization Activity (g polymer/ mmol Al * hr) |
| --- | --- | --- | --- |
| KA-108/$[CPh_3][B(C_6F_5)_4]$ | 158.3 | 10 | 1028.3 |
| KA-108/$[CPh_3][B(C_6F_5)_4]$[2] | 163.5 | 10 | 6491.7 |
| KA-108/$[CPh_3][B(C_6F_5)_4]$[3] | 165.7 | 10 | 4530.3 |
| KB-139/$[CPh_3][B(C_6F_5)_4]$[2] | 159.0 | 10 | 840.4 |

[1]General polymerization conditions: borate activation: 160° C. as a setting temperature; 200 psig of C2; 200 µmol/L of catalyst concentration; PMAO-IP at 1 mmol/L as a scavenger. Trityl borate as a cocatalyst at B/Al = 0.525; 216 mL of toluene as solvent.
[2]The B/Al = 1.05.
[3]Ethylene and 1-octene copolymerization with 38 mL of 1-octene with B/Al = 1.05.

TABLE 4

Polymer Property Data[1]

| Catalyst/Cocatalyst | Mw(*10$^{-3}$) | Pd | m.p. |
| --- | --- | --- | --- |
| KA-108/$[CPh_3][B(C_6F_5)_4]$ | 251.7 | 8.3 | 133.9 |
| KA-108/$[CPh_3][B(C_6F_5)_4]$[2] | 164.7 | 2.9 | 133.4 |
| KA-108/$[CPh_3][B(C_6F_5)_4]$[3] | 77.8 | 2.4 | 107.1 |
| KB-139/$[CPh_3][B(C_6F_5)_4]$[2] | 557.2 | 2.2 | 134.4 |

[1]General polymerization conditions: trityl borate activation: 160° C. as a setting temperature; 200 psig of C2; 200 µmol/L of catalyst concentration; trityl borate as cocatalyst at B/Al = 0.52; PMAO-IP at 1 mmol/L as a scavenger; 216 mL of toluene as solvent.
[2]The B/Al = 1.05.
[3]Ethylene and 1-octene copolymerization with 38 mL of 1-octene with B/Al = 1.05. The Br/1000 C. is 19.5.

What is claimed is:

1. A process for polymerizing one or more $C_{2-8}$ olefins at a temperature from 20° C. to 120° C. and at a pressure from 15 to 4500 psig in the presence of a complex of the formula V:

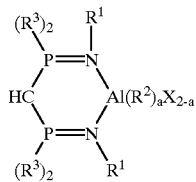

wherein each $R^1$ is independently selected from the group consisting of $C_{1-8}$ straight or branched alkyl radical or a $C_{6-12}$ cyclic aliphatic or aromatic radical; radicals of the formula $Si(R^4)_3$ wherein each $R^4$ is independently selected from the group consisting of $C_{1-8}$ alkyl and alkoxy radicals; $R^2$ is independently selected from the group consisting of $C_{1-8}$ alkyl radicals, X is a halogen atom and a is 1 or 2; and $R^3$ is selected from the group consisting of $C_{1-8}$ alkyl radicals and $C_{6-12}$ aromatic radicals which are unsubstituted or substituted with one or more halogen atoms or a $C_{1-4}$ alkyl radical and an activator selected from the group consisting of:

(i) aluminoxane compounds $R^{20}{}_2AlO(R^{20}AlO)_mAlR^{20}{}_2$ wherein each $R^{20}$ is independently selected from the group consisting of $C_{1-20}$ hydrocarbyl radical and m is from 5 to 30 to provide a molar ratio of aluminum in the activator to aluminum in the complex from 20:1 to 1000:1;

(ii) anions of the formula $[B(R^{18})_4]^-$ wherein each $R^{18}$ is independently selected from the group consisting of phenyl radicals which are unsubstituted or substituted by up to 5 substituents selected from the group consisting of a fluorine atom, a $C_{1-4}$ alkyl or alkoxy radical which is unsubstituted or substituted by a fluorine atom and a silyl radical of the formula $—Si(R^{19})_3$; wherein each $R^9$ is independently selected from the group consisting of a hydrogen atom and a $C_{1-4}$ alkyl radical; and an activator of the formula $[B(R^8)_3]$ wherein $R^{18}$ is as defined above, to provide a molar ratio of B:Al from 0.8 to 1.2; and (iii) a mixture of (i) and (ii) above.

2. A process for polymerizing one or more $C_{2-8}$ olefins at a temperature from 120° C. to 250° C. and at a pressure from 15 to 4500 psig in the presence of a complex of the formula V:

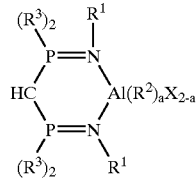

wherein each $R^1$ is independently selected from the group consisting of $C_{1-8}$ straight or branched alkyl radical or a $C_{6-12}$ cyclic aliphatic or aromatic radical; radicals of the formula $Si(R^4)_3$ wherein each $R^4$ is independently selected from the group consisting of $C_{1-8}$ alkyl and alkoxy radicals; $R^2$ is independently selected from the group consisting of $C_{1-8}$ alkyl radicals, X is a halogen atom and a is 1 or 2; and $R^3$ is selected from the group consisting of $C_{1-8}$ alkyl radicals and $C_{6-12}$ aromatic radicals which are unsubstituted or substituted with one or more halogen atoms or a $C_{1-4}$ alkyl radical and an activator selected from the group consisting of:

(i) aluminoxane compounds $R^{20}{}_2AlO(R^{20}AlO)_mAlR^{20}{}_2$ wherein each $R^{20}$ is independently selected from the group consisting of $C_{1-20}$ hydrocarbyl radical and m is from 5 to 30 to provide a molar ratio of aluminum in the activator to aluminum in the complex from 20:1 to 1000:1;

(ii) anions of the formula $[B(R^{18})_4]^-$ wherein each $R^{18}$ is independently selected from the group consisting of phenyl radicals which are unsubstituted or substituted by up to 5 substituents selected from the group consisting of a fluorine atom, a $C_{1-4}$ alkyl or alkoxy radical which is unsubstituted or substituted by a fluorine atom and a silyl radical of the formula $—Si(R^{19})_3$; wherein each $R^{19}$ is independently selected from the group consisting of a hydrogen atom and a $C_{1-4}$ alkyl radical; and an activator of the formula $[B(R^{18})_3]$ wherein $R^{18}$ is as defined above, to provide a molar ratio of B:Al from 0.8 to 1.2; and (iii) a mixture of (i) and (ii) above.

3. A process for polymerizing one or more $C_{2-8}$ olefins at a temperature from 20° C. to 120° C. and at a pressure from 15 to 4500 psig in the presence of a complex of formula IV:

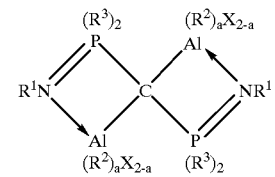

wherein each $R^1$ is independently selected from the group consisting of $C_{1-8}$ straight or branched alkyl radical or a $C_{6-12}$ cyclic aliphatic or aromatic radical; radicals of the formula $Si(R^4)_3$ wherein each $R^4$ is independently selected from the group consisting of $C_{1-8}$ alkyl and alkoxy radicals; $R_2$ is independently selected from the group consisting of $C_{1-8}$ alkyl radicals, X is a halogen atom and a is 1 or 2; and $R^3$ is selected from the group consisting of $C_{1-8}$ alkyl radicals and $C_{6-12}$ aromatic radicals which are unsubstituted or substituted with one or more halogen atoms or a $C_{1-4}$ alkyl radical and an activator selected from the group consisting of:

(i) aluminoxane compounds $R^{20}{}_2AlO(R^{20}AlO)_mAlR^{20}{}_2$ wherein each $R^{20}$ is independently selected from the group consisting of $C_{1-20}$ hydrocarbyl radical and m is from 5 to 30 to provide a molar ratio of aluminum in the activator to aluminum in the complex from 20:1 to 1000:1;

(ii) anions of the formula $[B(R^{18})_4]^-$ wherein each $R^{18}$ is independently selected from the group consisting of phenyl radicals which are unsubstituted or substituted by up to 5 substituents selected from the group consisting of a fluorine atom, a $C_{1-4}$ alkyl or alkoxy radical which is unsubstituted or substituted by a fluorine atom and a silyl radical of the formula $—Si(R^{19})_3$; wherein each $R^{19}$ is independently selected from the group consisting of a hydrogen atom and a $C_{1-4}$ alkyl radical; and an activator of a formula $[B(R^{18})_3]$ wherein $R^{18}$ is as defined above, to provide a molar ratio of B:Al from 0.4 to 1.2; and (iii) a mixture of (i) and (ii) above.

4. A process for polymerizing one or more $C_{2-8}$ olefins at a temperature from 120° C. to 250° C. and at a pressure from 15 to 4500 psig in the presence of a complex of formula IV:

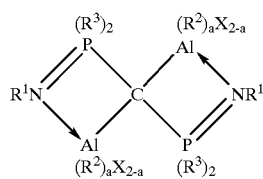

wherein each $R^1$ is independently selected from the group consisting of $C_{1-8}$ straight or branched alkyl radical or a $C_{6-12}$ cyclic aliphatic or aromatic radical; radicals of the formula $Si(R^4)_3$ wherein each $R^4$ is independently selected from the group consisting of $C_{1-8}$ alkyl and alkoxy radicals; $R^2$ is independently selected from the group consisting of $C_{1-8}$ alkyl radicals, X is a halogen atom and a is 1 or 2; and $R^3$ is selected from the group consisting of $C_{1-8}$ alkyl radicals and $C_{6-12}$ aromatic radicals which are unsubstituted or substituted with one or more halogen atoms or a $C_{1-4}$ alkyl radical and an activator selected from the group consisting of:

(i) aluminoxane compounds $R^{20}_2AlO(R^{20}AlO)_mAlR^{20}_2$ wherein each $R^{20}$ is independently selected from the group consisting of $C_{1-20}$ hydrocarbyl radical and m is from 5 to 30 to provide a molar ratio of aluminum in the activator to aluminum in the complex from 20:1 to 1000:1;

(ii) anions of the formula $[B(R^{18})_4]^-$ wherein each $R^{18}$ is independently selected from the group consisting of phenyl radicals which are unsubstituted or substituted by up to 5 substituents selected from the group consisting of a fluorine atom, a $C_{1-4}$ alkyl or alkoxy radical which is unsubstituted or substituted by a fluorine atom and a silyl radical of the formula $—Si(R^{19})_3$; wherein each $R^{19}$ is independently selected from the group consisting of a hydrogen atom and a $C_{1-4}$ alkyl radical; and an activator of the formula $[B(R^{18})_3]$ wherein $R^{18}$ is as defined above, to provide a molar ratio of B:Al from 0.4 to 1.2; and (iii) a mixture of (i) and (ii) above.

* * * * *